(12) United States Patent
Koppert

(10) Patent No.: US 10,258,703 B2
(45) Date of Patent: Apr. 16, 2019

(54) DEVICE AND METHOD FOR INTRODUCING ELECTROMAGNETIC RADIATION EFFICIENTLY INTO SOIL

(71) Applicant: Agritron B.V., Waddinxveen (NL)

(72) Inventor: Arie Leendert Koppert, Monster (NL)

(73) Assignee: Koppert Machine En Zonen B.V., Monster (NL)

( * ) Notice: Subject to any disclaimer, the term of this patent is extended or adjusted under 35 U.S.C. 154(b) by 0 days.

(21) Appl. No.: 15/511,511

(22) PCT Filed: Sep. 17, 2015

(86) PCT No.: PCT/NL2015/050642
§ 371 (c)(1),
(2) Date: Mar. 15, 2017

(87) PCT Pub. No.: WO2016/043585
PCT Pub. Date: Mar. 24, 2016

(65) Prior Publication Data
US 2017/0239380 A1 Aug. 24, 2017

(30) Foreign Application Priority Data

Sep. 17, 2014 (NL) ...................................... 2013478

(51) Int. Cl.
*A61L 2/12* (2006.01)
*A01M 21/04* (2006.01)
(Continued)

(52) U.S. Cl.
CPC .................. *A61L 2/12* (2013.01); *A01G 7/00* (2013.01); *A01G 22/00* (2018.02); *A01M 21/04* (2013.01)

(58) Field of Classification Search
CPC ................................ A61L 2/12; A01M 21/04
See application file for complete search history.

(56) References Cited

U.S. PATENT DOCUMENTS

| 2002/0046474 A1* | 4/2002 | Novak ...................... A61L 2/12 34/259 |
| 2003/0215354 A1 | 11/2003 | Clark et al. |
| 2013/0240507 A1* | 9/2013 | Kimrey, Jr. .............. H05B 6/70 219/702 |

FOREIGN PATENT DOCUMENTS

| DE | 2306061 A1 | 8/1973 |
| DE | 10037078 A1 | 2/2002 |
| NL | 2008078 C | 7/2013 |

OTHER PUBLICATIONS

Machine translation of NL 2008078 (Year: 2013).*

* cited by examiner

*Primary Examiner* — Timothy C Cleveland
(74) *Attorney, Agent, or Firm* — Rudy J. Ng; Bret E. Field; Bozicevic, Field & Francis LLP

(57) ABSTRACT

The invention relates to a device for treating soil with electromagnetic radiation, comprising: a magnetron antenna (9) for generating microwave radiation with a relatively high frequency; a wave guide (16) connected to the output of the magnetron antenna (9); downward directed tubular members (18, 19) connected to the wave guide (16); a manifold (17) arranged between the two tubular members (18, 19) and the wave guide (16); a tuner unit (26) arranged on the wave guide (16); and cooling means (22, 22', 22") for cooling the electromagnetic radiation reflected by the soil. The invention also relates to a cable (24) provided with a single high-voltage cable and one or more low-voltage cables and/or a number of optical cables which are arranged in a shared cable. The invention finally relates to a method for disinfecting soil, wherein a magnetron (9) placed on a vehicle is moved over the soil, wherein the radiation reflected by the soil is minimized by tuning the wave guide (16) connected to the magnetron (9), and wherein the (Continued)

minimized reflected radiation is absorbed by a water load which is connected to one or two water tanks (22', 22") which are placed on the vehicle and which hold the temperature of the water within predetermined limits.

14 Claims, 5 Drawing Sheets

(51) Int. Cl.
*A01G 22/00* (2018.01)
*A01G 7/00* (2006.01)

DEVICE AND METHOD FOR INTRODUCING ELECTROMAGNETIC RADIATION EFFICIENTLY INTO SOIL

As already set forth in the Netherlands application NL2008078, the disinfection of soil, particularly in horticulture, is no simple matter. In this earlier patent application it has already been proposed to introduce electromagnetic (EM) radiation into the soil in order to disinfect the soil.

It has been found that, at the relatively high power that is desirable to enable travel over horticultural soil with sufficient speed, the reflected EM waves are an important factor.

The device described in the above stated Netherlands patent application is found to become too hot and lacks a cooling for the purpose of sufficient cooling of the radiation reflected by the soil.

The American patent publication US 2003/2153554 describes a device for disinfecting soil, wherein the soil is guided underneath the magnetron antennas on a conveyor, which is therefore not a very practical method.

In the international search report DE2306061 and DE10037078 are also cited as background to the prior art.

The present invention provides a device for treating soil with EM waves, comprising a magnetron antenna for generating EM microwaves with a relatively high frequency and a wave guide connected to the output of the magnetron antenna.

According to the present invention the coupling between the wave guide and the tubular members can first be precisely adjusted, for instance by arranging adjusting plates between the wave guide and the T-piece. Depending on the composition and/or moistness of the soil, a tuner unit can then be used to further limit the reflected power as much as possible.

The reflected power is preferably absorbed by a so-called water load, i.e. a space in which water is received in order to discharge the reflected energy as heat. It is recommended for this purpose that the cooling load is connected to cooling tanks placed on the vehicle.

In order to make the vehicle manageable a new cable has been developed, within the sheathing of which high-voltage, optical fibre and low-voltage cables are guided, whereby the weight of the cable is reduced by half.

In order to reduce ambient radiation (and to comply with the standards therefor) a base plate is preferably arranged around the funnel-shaped outer ends of the tubular members.

The present invention also comprises a method for driving a vehicle with magnetron antenna over the soil at sufficient speed.

Further advantages and features of the present invention will be elucidated on the basis of the following description of the preferred embodiment thereof, wherein reference is made to the drawings, wherein.

Figure 1:
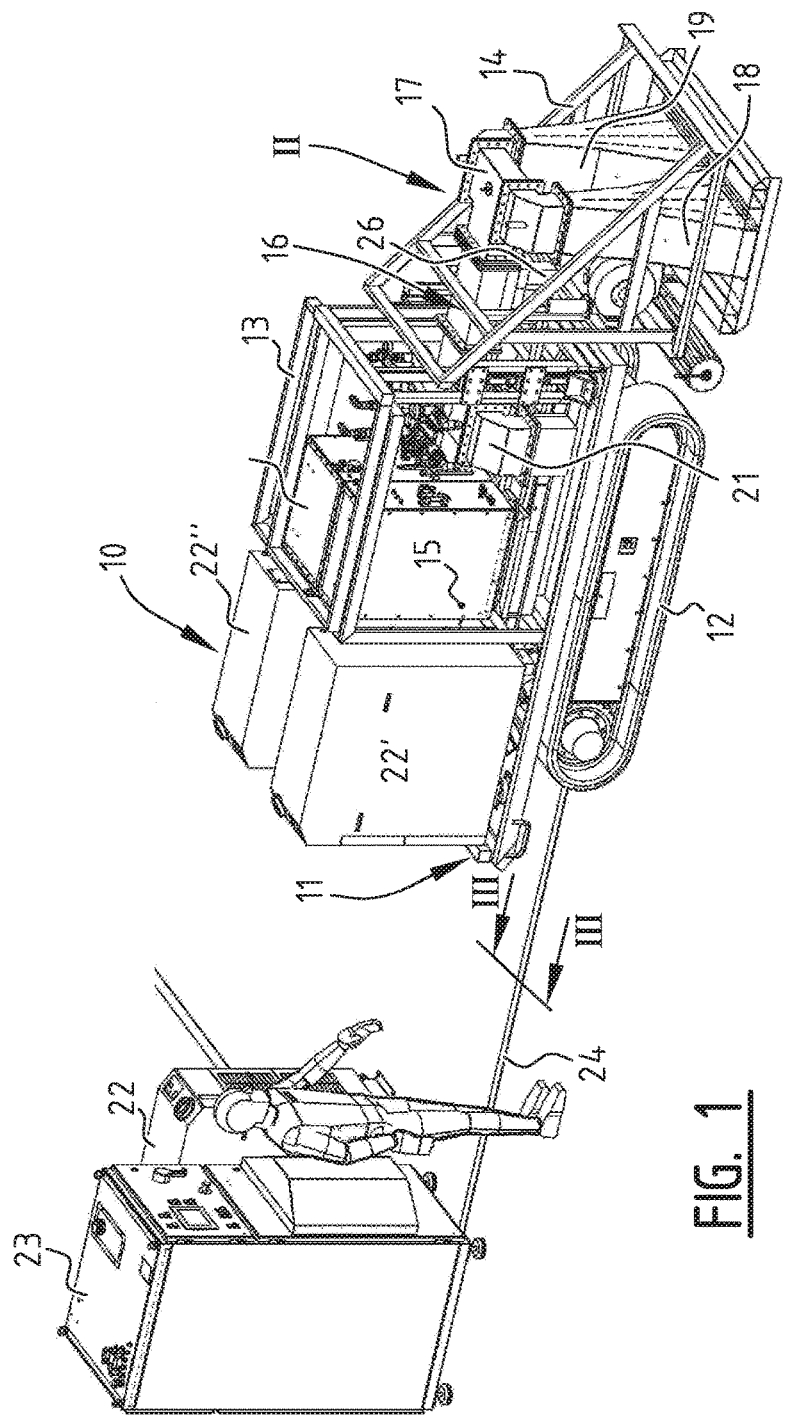
FIG. 1 shows a schematic view of a preferred embodiment of the device according to the invention.

Device 10 (FIG. 1) comprises a chassis 11 under which caterpillar tracks 12 are arranged and on which a first frame 13 and a second frame 14 are mounted. Disposed on first frame 13 are magnetron 9 and control 15 therefor. The electromagnetic waves are guided in wave guide 16 via T-piece 17 to distributing horns 18, 19, which distributing horns 18, 19 are arranged on second frame 14. Situated to the side of the location where the magnetron is arranged is a water load 21 which is connected via conduits (not shown) to water tanks to be placed on the rear side of the chassis. A water tank 22 which is removable from the chassis is shown in FIG. 1 adjacently of a power supply 23. Power supply 23 is connected via a cable 24 to the magnetron control boxes 15.

Also shown on the underside of wave guide 16 is a tuner unit 26 which, using retractable and extendable rods, can tune the wave guide, which is formed by waveguide 16, T-piece 17 and horns 18 and 19, as well as possible to the composition and moistness of the ground. Also placed between waveguide 16 and T-piece 17 are a number of adjusting plates 27 which adjust the dimensions as accurately as possible to the ground and the size of the wave guides, whereby only one tuner unit 26 is required.

Also shown in FIG. 1 is a base plate on the downward directed funnel-shaped outer end of distributing horns 18, 19, which base plate 31 has a profiled form which experimentally reduces the power of the EM waves all around the outer ends.

A high voltage of 19,000 V can be transmitted to magnetron antenna 9 through cable 24, as well as control signals and three-phase electrical power supply of 400 V. The energy of 100 kW at a frequency of 915 Megahertz (MHZ) is introduced into the ground via the magnetron antenna in the distributing horns.

It has been found that a sufficiently bactericidal effect is obtained to a depth of 30 cm at a travel speed of 20 cm per minute.

The wave impedance can be modified to the wave impedance of the soil using a tuner. Reflection of less than 10 percent of the generated power has been found to be possible. The reflected power heats the water in the water load. The temperature of the water in cooling reservoirs 22, 22', 22" which are placed on chassis 11 has to be kept within a range of 18-25° C. The cooling reservoirs are preferably provided with a built-in pump to allow circulation of the water (or other cooling liquid). If the tuning is insufficient, EM waves with too much energy will be reflected and result in excessive heating of the water.

Figure 2:
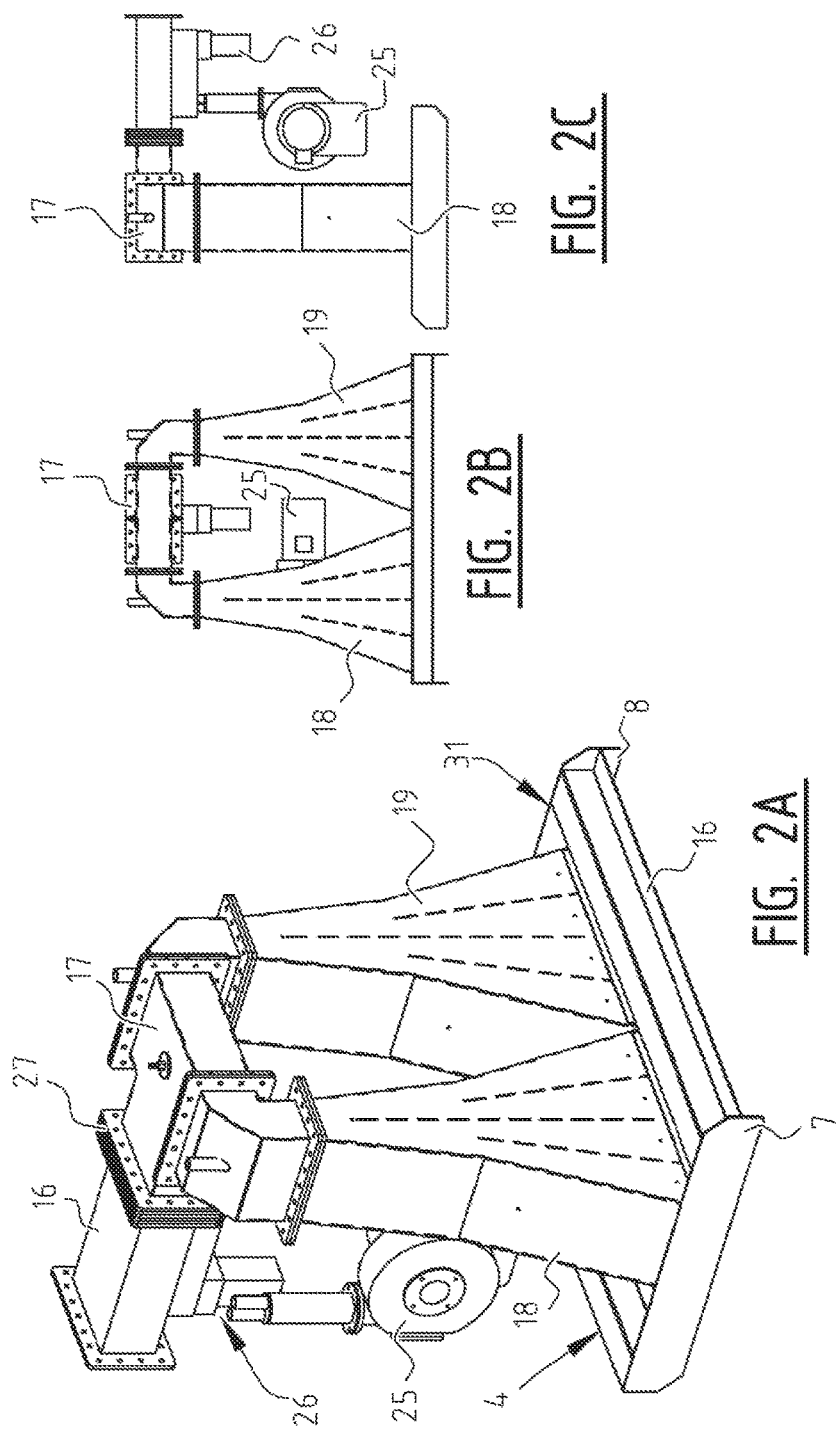
FIG. 2A, 2B, 2C show respectively a perspective view, a front view and a side view of detail II of FIG. 1.

Distributing horns 18, 19 and T-piece 17, and tuner 26 are shown particularly in the embodiment of FIG. 2A, 2B, 2C.

Base plate 31 is provided with two flanges which connect laterally to distributing horns 18, 19 and preferably cut to at least some extent into the soil in order to increase the shielding action. Formed on the front and rear side by curved plates 4, 6 are chambers in which for instance slate or other material which absorbs EM waves can be received.

Wave guide 16 is held at overpressure by an air pump (not shown). A partition of material allowing passage of EM waves 25, for instance teflon, is preferably arranged between wave guide 16 and manifold 17. Manifold 17 and horns 18 and 19 are likewise held at overpressure by an air pump. The overpressure serves to prevent the formation of moisture and sparking in the waveguides in which the EM waves propagate. FIG. 2A also shows adjusting plates 27.

Figure 3:
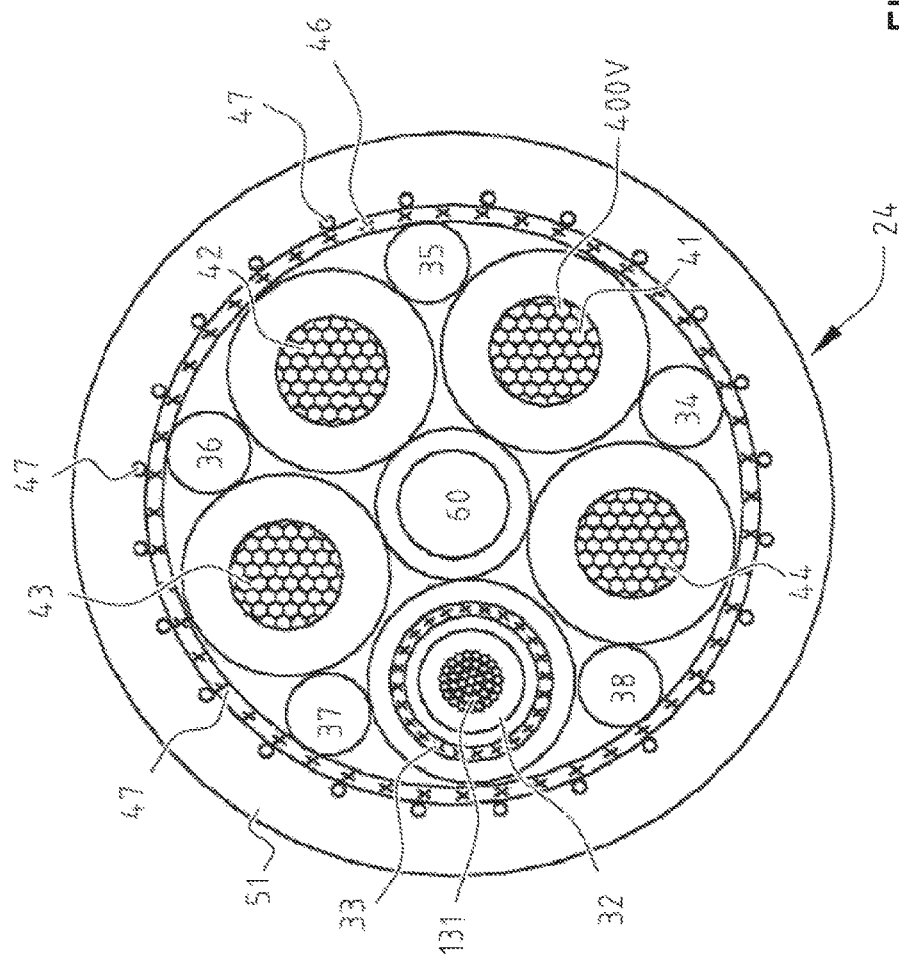
FIG. 3 shows a cross-sectional view of the cable of the exemplary embodiment of FIG. 1.

So that cable 24 can be kept light in weight it comprises a high-voltage core 131 (FIG. 3) assembled from a number of strands, around which lie insulation 32 and a shielding unit 33, as well as five glass fibre cores 34, 35, 36, 37, 38 which are used for control signals, and four cores 41, 42, 43, 44 for transmitting low voltage of 400 V in different phases, as well as an earth wire. Preferably arranged around a shielding sheath 46 is a Kevlar reinforcement 47 around which outer sheath 51 is placed. A pull relief 60, preferably of a strong material such as Kevlar, is arranged in the centre.

Figure 4:
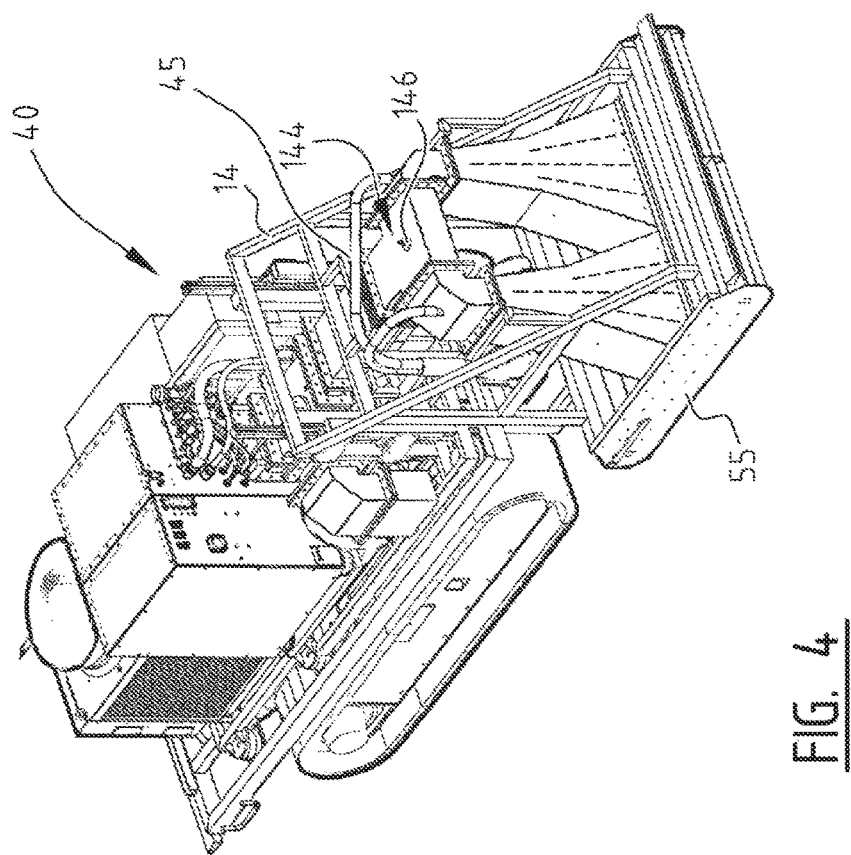
FIG. 4 shows a perspective view of a second preferred embodiment of a vehicle according to the present invention.
Figure 6:
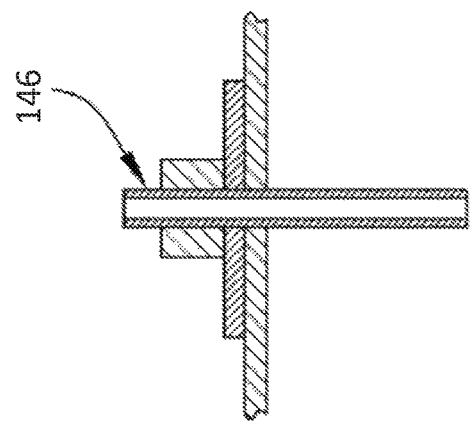
FIG. 6 shows a cross-sectional view of detail VI of FIG. 4.

In a second preferred embodiment according to the present invention (FIG. 4) a frame 41 on which horns are arranged on a manifold 144 is arranged on a vehicle 40. Manifold 144 is connected by means of adjusting plates 45 to the magnetron on vehicle 40. Present in the distributing horn as in the embodiment of FIG. 1 is a rod 146 which distributes the microwave radiation from the magnetron antenna substantially equally between horns. In the present embodiment rod 146 takes a hollow form (see FIG. 6) so that it is connected to the water cooling in order to prevent heating thereof.

Figure 5:
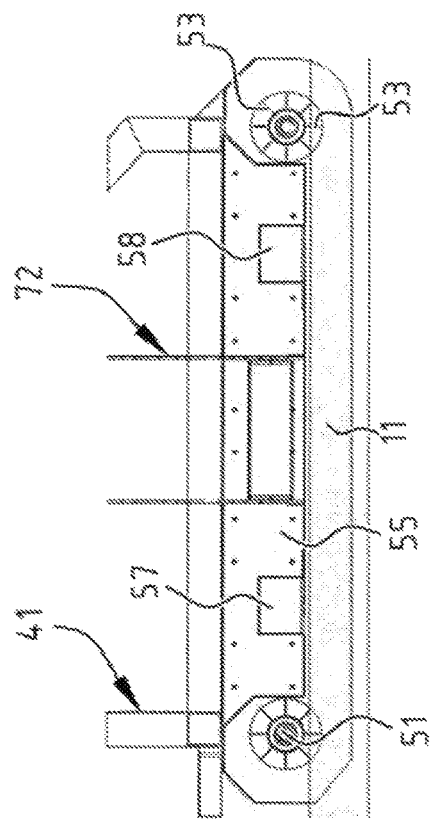
FIG. 5 shows a cross-section along the line V-V in FIG. 4.

As shown in FIG. 5, the microwave radiation to the front and rear is contained by means of rotors arranged on shafts 51, 52 and co-rotating in the direction of travel and having shielding plates 53 which protrude each in turn into the ground U.

Also shown in FIG. 5 are side plates 55, 56 and optional cavities 58, wherein cavities 58 serve to further absorb radiation. Side plates 55 cut into the ground to some extent so that some radiation can enter the ground laterally, this being advantageous for instance when travelling along uprights of a greenhouse, so that the soil in the line between the uprights is also disinfected.

Further advantages, features and details of the present invention will be elucidated on the basis of the following claims. The above described preferred embodiments are not limitative for the scope of protection of the present patent application; the rights sought are defined by the following claims, within the scope of which many modifications can be envisaged.

The invention claimed is:

1. A device for treating soil with electromagnetic radiation, comprising:
    a magnetron antenna for generating microwave radiation;
    a wave guide connected to an output of the magnetron antenna;
    two downward directed tubular members connected to the wave guide;
    a manifold arranged between the two tubular members and the wave guide;
    a distributing rod provided in the manifold for distributing the microwave radiation from the magnetron antenna substantially equally between the two tubular members;
    a tuner unit arranged on the wave guide; and
    a cooler comprising a space filled with water coupled to the waveguide for absorbing the electromagnetic radiation reflected by the soil.

2. The device as claimed in claim 1, wherein one or more reservoirs with cooling liquid are arranged on a vehicle and cooling tanks are also coupled to the space filled with water so that the temperature is kept within a predetermined temperature range.

3. The device as claimed in claim 2, wherein the distributing rod is connected to the cooler.

4. The device as claimed in claim 1, wherein at least one base plate is arranged on either side of the downward directed end of the tubular members.

5. The device as claimed in claim 1, further comprising a vehicle for supporting the device, wherein the vehicle and the device are coupled via a combined cable for high voltage, optical signals and a power supply.

6. The device as claimed in claim 5, wherein the cable also comprises a number of low-voltage cables for a low voltage.

7. The device as claimed in claim 5, wherein the high-voltage cable has a separate shielding sheath and the high-voltage cable and other cables are received in a shared sheathing.

8. The device as claimed in claim 1, provided with one or more air pumps for holding the wave guide and/or the manifold and/or the tubular member at overpressure.

9. The device as claimed in claim 4, wherein the base plate is provided with one or more spaces in which material absorbing EM waves is arranged.

10. The device as claimed in claim 4, wherein the base plate is provided on one or both sides with a flange which protrudes downward into the ground.

11. A method for disinfecting soil, comprising:
    moving a device on a vehicle over the soil, wherein the device comprises:
        a magnetron antenna for generating microwave radiation;
        a wave guide connected to an output of the magnetron antenna;
        two downward directed tubular members connected to the wave guide;
        a manifold arranged between the two tubular members and the wave guide;
        a distributing rod provided in the manifold for distributing the microwave radiation from the magnetron antenna substantially equally between the two tubular members;
        a tuner unit arranged on the wave guide; and
        a cooler comprising a space filled with water coupled to the waveguide for absorbing electromagnetic radiation reflected by the soil,
    wherein the radiation reflected by the soil is minimized by tuning the wave guide connected to the magnetron, and wherein the minimized reflected radiation is absorbed by the water which is connected to one or two water tanks which are placed on the vehicle and which hold the temperature of the water within predetermined limits.

12. The method as claimed in claim 11, wherein the frequency of the magnetron amounts to about 915 MHZ.

13. The method as claimed in claim 11, wherein the power generated in the magnetron amounts to about 100 kW.

14. The method as claimed in claim 11, wherein the device further comprises:
    a cable provided with a single high-voltage cable and one or more low-voltage cables and/or a number of optical cables which are arranged in a shared sheathing.

* * * * *